US011653867B2

(12) United States Patent
Jain et al.

(10) Patent No.: US 11,653,867 B2
(45) Date of Patent: *May 23, 2023

(54) CONTACTLESS ELECTRIC CARDIOGRAM SYSTEM

(71) Applicant: RR Sequences Inc., Montreal (CA)

(72) Inventors: Deepak Bobby Jain, Brossard (CA); Joshua Weeks, Montreal (CA); David Nadezhdin, Montreal (CA); Jean-Francois Asselin, Brossard (CA)

(73) Assignee: RR SEQUENCES INC., Montreal (CA)

( * ) Notice: Subject to any disclaimer, the term of this patent is extended or adjusted under 35 U.S.C. 154(b) by 211 days.

This patent is subject to a terminal disclaimer.

(21) Appl. No.: 17/164,694

(22) Filed: Feb. 1, 2021

(65) Prior Publication Data

US 2022/0007984 A1    Jan. 13, 2022

Related U.S. Application Data

(63) Continuation of application No. 16/037,239, filed on Jul. 17, 2018, now Pat. No. 10,939,840, which is a
(Continued)

(51) Int. Cl.
*A61B 5/282* (2021.01)
*A61B 5/00* (2006.01)
(Continued)

(52) U.S. Cl.
CPC ............ *A61B 5/282* (2021.01); *A61B 5/1114* (2013.01); *A61B 5/276* (2021.01); *A61B 5/277* (2021.01);
(Continued)

(58) Field of Classification Search
CPC ......... A61B 5/277; A61B 5/308; A61B 5/318; A61B 5/0006; A61B 2562/0214
See application file for complete search history.

(56) References Cited

U.S. PATENT DOCUMENTS

2010/0262026 A1* 10/2010 Meftah ................ A61B 5/6887
600/509
2011/0288605 A1* 11/2011 Kaib ..................... A61B 5/7221
607/5

(Continued)

*Primary Examiner* — Michael W Kahelin
(74) *Attorney, Agent, or Firm* — PCFB LLC

(57) ABSTRACT

A system for providing a standard electrocardiogram (ECG) signal for a human body using contactless ECG sensors for outputting to exiting medical equipment or for storage or viewing on a remote device. The system comprises a digital processing module (DPM) adapted to connect to an array of contactless ECG sensors provided in a fabric or the like. A selection mechanism is embedded into the DPM which allows the DPM to identify body parts using the ECG signals of the different ECG sensors and select for each body part the best sensor lead. The DPM may then produce the standard ECG signal using the selected ECG signals for the different body parts detected. The system is adapted to continuously re-examine the selection to ensure that the best leads are selected for a given body part following a movement of the body part, thereby, allowing for continuous and un-interrupted ECG monitoring of the patient.

18 Claims, 10 Drawing Sheets

Related U.S. Application Data continuation of application No. 14/893,293, filed as application No. PCT/CA2015/050938 on Sep. 23, 2015, now Pat. No. 10,052,042.

(60) Provisional application No. 62/206,542, filed on Aug. 18, 2015, provisional application No. 62/054,189, filed on Sep. 23, 2014.

(51) Int. Cl.
*A61B 5/11* (2006.01)
*A61B 5/276* (2021.01)
*A61B 5/302* (2021.01)
*A61B 5/318* (2021.01)
*A61B 5/327* (2021.01)
*A61B 5/339* (2021.01)
*A61B 5/308* (2021.01)
*A61B 5/277* (2021.01)
*A61B 5/316* (2021.01)

(52) U.S. Cl.
CPC .............. *A61B 5/302* (2021.01); *A61B 5/308* (2021.01); *A61B 5/318* (2021.01); *A61B 5/327* (2021.01); *A61B 5/339* (2021.01); *A61B 5/6844* (2013.01); *A61B 5/7221* (2013.01); *A61B 5/0006* (2013.01); *A61B 5/316* (2021.01); *A61B 2562/0214* (2013.01); *A61B 2562/046* (2013.01); *A61B 2562/164* (2013.01)

(56) References Cited

U.S. PATENT DOCUMENTS

2015/0241505 A1* 8/2015 Freeman ................ A61B 5/746 324/538
2016/0228063 A1* 8/2016 Fukuyama ........... A61B 5/6887

* cited by examiner

CONTACTLESS ELECTRIC CARDIOGRAM SYSTEM

CROSS-REFERENCE TO RELATED APPLICATIONS

This application is a continuation of U.S. application Ser. No. 16/037,239, filed on Jul. 17, 2018, which is a continuation of U.S. application Ser. No. 14/893,293, filed on Nov. 23, 2015, which application is a national phase entry under 35 U.S.C. § 371 of International Patent Application PCT/CA2015/050938, filed Sep. 23, 2015, designating the United States of America and published in English as International Patent Publication WO 2016/044933, which claims priority to U.S. Provisional Patent Application No. 62/054,189 filed on Sep. 23, 2015 and U.S. Provisional Patent Application No. 62/206,542 filed on Aug. 18, 2015, the disclosures of each of which are hereby incorporated herein in their entirety by this reference.

BACKGROUND

(a) Field

The subject matter generally relates to electro-cardiogram systems.

(b) Related Prior Art

Electrocardiograms (hereinafter ECG's) are the only reliable measurement of heart rate, arrhythmia detection, resting ECG abnormalities that necessitate mandatory further testing, changes from previous ECG's.

The ECG is one of the basic diagnostic and follow up screening tools used in medicine for a large number of cardiac and non-cardiac diseases. While the standard 12-lead electrocardiogram holds a wealth of information, it only captures data for 10 seconds. Long term monitoring with multiple leads provides even more information and leads to better access to changes in the electrocardiogram.

The lack of long term monitoring is an important medical problem for multiple reasons. The lack of a baseline electrocardiogram in a patient's file often results in confusion and needless additional exams in patients who have ECGs done for the first time which are normal for them, but abnormal according to established criteria. Often, if an old ECG, even one from 10 years prior, is available that is the same as the perceived abnormal ECG, no further exams are required. In other words, the ability to compare a current ECG to an old one is of immense medical value. An unchanged one results in fewer examinations.

Traditional electrocardiographic measurement systems that rely on contact electrodes (electrodes which form a galvanic connection with the patient's body) present challenges when ECG monitoring is required immediately, unobtrusively or frequently. Traditional contact electrodes require placement by a trained healthcare provider on a clean, prepared skin surface to ensure accurate location (and therefore morphology) and signal quality. Limitations of standard wet gel contact electrode placement include placing them on the body correctly and removing them within their time limit to avoid skin reactions.

Apart from their inability to provide long term monitoring, their availability is also limited as discussed below.

Ideally, ECGs should be performed on all patients as part of the routine medical visit, especially if the patient has symptoms that necessitate medical attention. However, the availability of the test is limited. Their availability is limited due to the cost of the ECG equipment and the un-availability of the technicians needed to perform the test on patients to put the leads on the patient correctly. With respect to ECG costs, most physicians do not invest in having the test on site. Even in hospitals, telemetry units are limited to about 6 to 10 units located outside of the intensive care units for the entire patients in a large hospital.

Another disadvantage is that standard electrodes have multiple problems that limit proper and widespread use of the ECG. These problems are:
1. The electrodes react with the skin due to the metal, gel, and adhesive reactions, which requires multiple changes during a hospital stay;
2. The lack of knowledge required to correctly place the electrodes;
3. The time for placing the electrodes;
4. The complications associated with extended monitoring such as when the electrodes fall off regularly due to sweat, patient's movement, improper placement, etc;
5. ECG's derived using standard electrodes are prone to muscular artifacts that result in false ECG's.

A further disadvantage is that the electrocardiogram obtained with standard electrodes is labor and material intensive. Even a telemetry unit can take, in certain cases, upwards of 2-3 hours per day per patient of nursing time to install and re-install standard electrodes.

Yet a further disadvantage is that ECGs are a source of nosocomial infection spread in hospitals because of wires and their contact with nursing and hospital staff, and frequent nursing attention to the electrodes.

Accordingly, there is a need in the market for a system and method which address the shortcomings addressed above.

SUMMARY

The embodiments describe an ECG system which allows for frequent, inexpensive and accessible recording of ECG data from any patient or person easily, unobtrusively and quickly by eliminating the need to manually identify and prepare areas on the patient's body for contact sensors and to place sensors on those areas. The described system circumvents issues associated with contact electrodes by being contactless and by allowing multi-hour, multiple lead monitoring on a daily basis and for life.

In one aspect, there is provided a medical apparatus (aka DPM) for providing electrocardiogram (ECG) signals for a human body using contactless ECG sensors, the medical apparatus comprising: an input adapted to receive contactless ECG signals from an array of contactless ECG sensors; a processor adapted to perform a selection process including: detecting body parts located in proximity of the array of contactless ECG sensors; associating a group of contactless ECG sensors with each detected body part; selecting from each group a contactless ECG sensor having a highest signal quality; the processor being adapted to produce a standard ECG signal based on the received contactless ECG signal of each selected contactless ECG sensor; and an output for sending the standard ECG signal.

The Medical apparatus may be a lightweight portable device that weighs less than 2 lbs.

In an embodiment, the selection process further comprises the steps of: obtaining a body outline of the human body using the contactless ECG signals associated with the contactless ECG sensors located in proximity of the human body; determining a position of the human body on the array of contactless ECG sensors; dividing the contactless ECG sensors into groups and associating each group to a body part using the body outline and the position of the human body; and from each group, selecting the contactless ECG sensor providing the contactless ECG signal having the highest quality.

In an embodiment, the processor may identify the contactless ECG sensors that are located in close proximity to the human body by measuring an impedance between each contactless ECG sensor and the human body.

In another embodiment, the medical apparatus may be adapted to select another contactless ECG sensor for a given body part following a movement of the human body with respect to the array of contactless ECG sensors. In a further embodiment, the processor may be adapted to re-run the selection process continuously to perform the selection of the other contactless ECG sensor. The processor may also be adapted to continuously monitor a signal quality of the selected contactless ECG sensor associated with each body part to re-run the selection process when the signal quality drops beyond a given threshold.

The medical apparatus may comprise different operation modes comprising: a contactless mode which outputs a first standard ECG signal resulting from the contactless ECG signals; a hybrid mode which outputs a second standard ECG signal resulting from the contactless ECG signals and conventional ECG signals received from conventional contact electrodes; and a bypass mode which outputs a third standard ECG signal resulting from conventional ECG signals received from conventional contact electrodes.

The medical apparatus may further comprise an automatic gain control mechanism adapted to control relative impedance differences between different contactless ECG sensors and absolute impedance of each contactless ECG sensor to the human body due to a difference in distance or clothing materials between each contactless ECG sensor and the human body.

A wired/wireless data port may be provided for transmitting the standard ECG signal to a remote device over a data network.

In another aspect, a system for providing electrocardiogram (ECG) signals for a human body using contactless ECG sensors, the system comprising: a senor pad comprising an array of contactless ECG sensors; a processor operatively connected to the sensor pad and adapted to receive contactless ECG signals from the contactless ECG sensors and perform a selection process including: detecting body parts located in proximity of the array of contactless ECG sensors; associating a group of contactless ECG sensors with each detected body part; selecting from each group a contactless ECG sensor having a highest signal quality; the processor being adapted to produce a standard ECG signal based on the contactless ECG signal of each selected contactless ECG sensor; and an output for sending the standard ECG signal.

In an embodiment, the sensor pad comprises a grounding pad for placing in proximity of and at distance from the human body, the grounding pad being adapted to provide a capacitively coupled ground reference to the human body for reducing interference.

In another embodiment, the grounding pad may be driven with a feedback signal derived from the contactless ECG signals.

The system may further comprise a drive signal generator configured to feed the grounding pad with a high frequency signal that is outside of an ECG frequency band for determining the capacitively coupled ground reference for each contactless ECG sensor.

In an embodiment, the contactless ECG sensor may comprise: a capacitive electrode adapted to be capacitively coupled to the human body for outputting an electrical charge which is representative of an electrical cardiac activity; an electrodynamic sensor configured to detect and amplify the electrical charge produced by the capacitive electrode; and an electrode shield physically provided in proximity of the electrode for reducing a stray interference at an input of the electrodynamic sensor.

The contactless ECG sensor may me made of a flexible material.

In an embodiment, the sensor pad may be provided in a fabric with which the human body comes in contact.

In a further aspect, there is provided a method for providing electrocardiogram (ECG) signals for a human body using contactless ECG sensors, the method comprising: receiving contactless ECG signals from an array of contactless ECG sensors; detecting body parts located in proximity of the array of contactless ECG sensors; associating a group of contactless ECG sensors with each detected body part; selecting from each group a contactless ECG sensor having a highest signal quality; and producing a standard ECG signal based on the contactless ECG signal of each selected contactless ECG sensor.

The method may further comprise obtaining a body outline of the human body using the contactless ECG signals associated with the contactless ECG sensors located in proximity of the human body; determining a position of the human body on the array of contactless ECG sensor; dividing the contactless ECG sensors into groups and associate each group to a body part using the body outline and the position of the human body; and from each group, selecting the contactless ECG sensor providing the contactless ECG signal having the highest quality.

In an embodiment, the method further comprises identifying the contactless ECG sensors that are located in close proximity to the human body by measuring an impedance between each contactless ECG sensor and the human body.

The method may further repeat the steps of detecting to selecting continuously for selecting another contactless ECG sensor for a given body part following a movement of the human body with respect to the array of contactless ECG sensors. In on embodiment, it is possible to continuously monitor a signal quality of the selected contactless ECG sensor associated with each body part and repeat the steps of detecting to selecting for selecting another contactless ECG sensor for a given body part when the signal quality drops beyond a given threshold following a movement of the human body with respect to the array of contactless ECG sensors.

The following terms are defined below:

The term lead is intended to mean a difference in measured voltage between two locations on the human body that provide and show PQRSTU waveforms.

The term ECG lead is intended to mean a medically defined ECG signal based on a difference in measured voltage between two medically defined locations on the human body.

Standard ECG signal is an ECG signal that interfaces with existing medical equipment and conforms to ECG standards. A standard ECG signal may include a single rhythm strip or any number of standard medically defined ECG leads.

A rhythm strip is any lead that shows the rhythm between the PQRSTU waveforms. The rhythm strip does not require that the ECG signal be taken from the medically defined ECG locations.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

A system for providing a standard electrocardiogram (ECG) signal for a human body using contactless ECG sensors for outputting to exiting medical equipment (as well as to new/dedicated monitors, or for viewing on a display device associated with a computing device) or for storage or viewing on a remote/local device. The system comprises a digital processing module (DPM) adapted to connect to an array of contactless ECG sensors provided in a fabric or the like. A selection mechanism is embedded into the DPM which allows the DPM to identify body parts using the ECG signals of the different ECG sensors and select for each body part the best sensor lead. The DPM may then produce the standard ECG signal using the selected ECG signals for the different body parts detected. The system is adapted to continuously re-examine the selection to ensure that the best leads are selected for a given body part following a movement of the body part, thereby, allowing for continuous and un-interrupted ECG monitoring of the patient.

The present invention will be more readily understood by referring to the following examples which are given to illustrate the invention rather than to limit its scope.

Figure 1:
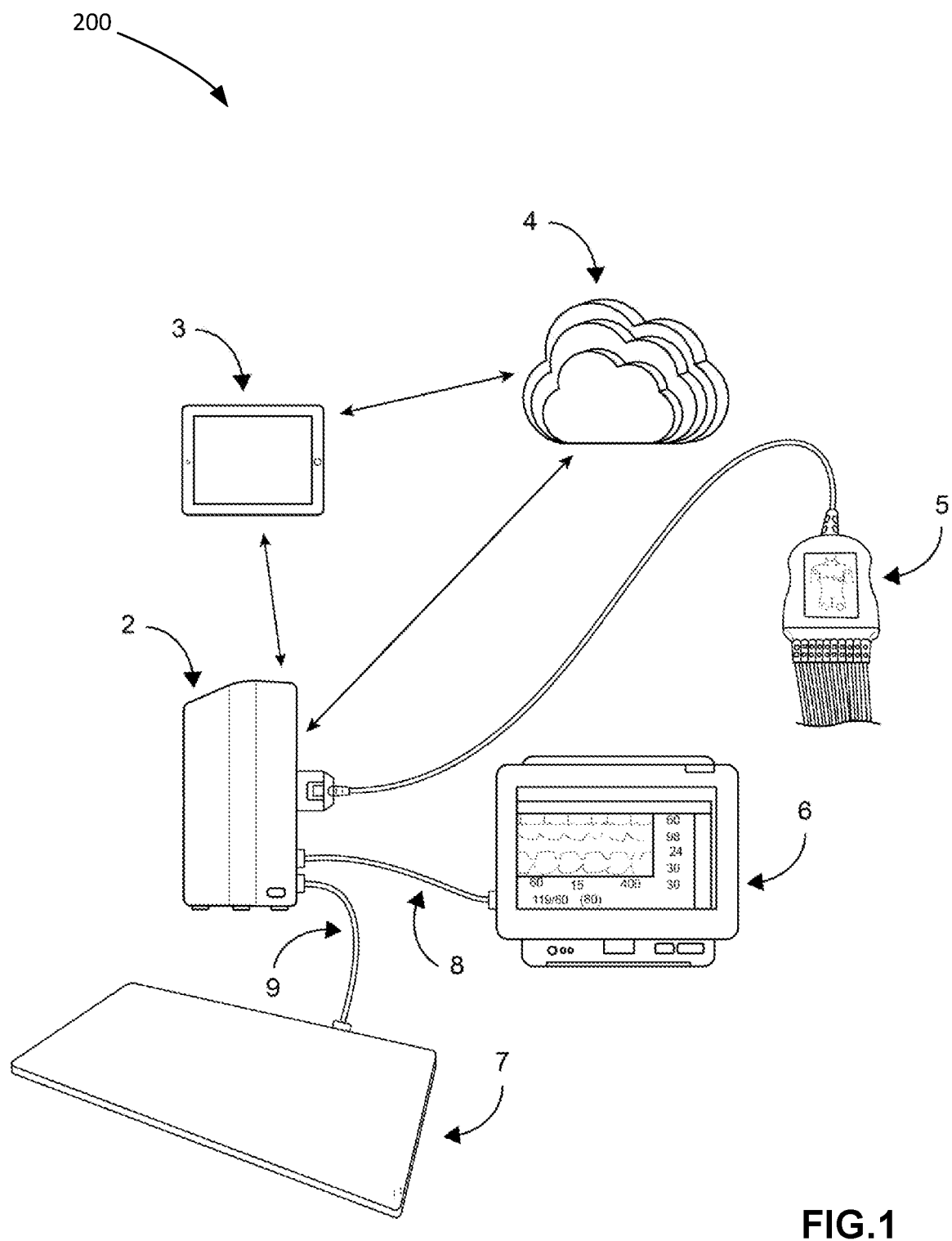
FIG. 1 is a block diagram of an exemplary ECG system in accordance with an embodiment.

Referring now to the drawings, FIG. 1 is a block diagram of an exemplary ECG system 200 in accordance with an embodiment. As shown in FIG. 1 the system 200 comprises an array of contactless sensors provided in a sensor pad 7 (in a non-limiting example of implementation), and a digital processing module (DPM) 2 which is operatively connected to the array of sensors using a cable 9 for obtaining sensor readings from the sensors provided in the pad 7. The DPM 2 may be configured to simultaneously record the electrophysiological activity of the heart (body surface potential map) as well as identify the best electrodes/sensors to output a standards ECG signal (+posterior precordials) into existing medical equipment (6). The DPM may be connected to a mobile device (3) or the cloud (4) via the internet or a data network to make the data readily available for doctors and in real-time so that doctors can quickly diagnose arrhythmic and ischemic changes detected by the DPM 2.

In a non-limiting example, the DPM 2 may be provided as a lightweight portable medical device which weighs about 2 lbs or less and may be carried around for performing the continuous ECG monitoring.

As stated above, the DPM 2 may be configured to produce an output signal which conforms to existing medical standards so that the output signal is identical to those that are acquired by a standard contact ECG system and may be viewed/read using existing medical equipment 6 in a plug and play manner (whereby no changes are to be made to the existing medical equipment to read and output the standard ECG signal received from the DPM). The DPM 2 may include a data output plug adapted to receive a standard cable (8) to output a signal that be simultaneously read using an existing medical equipment 6. The DPM 2 may also be able to simultaneously record contact ECG information if a standard trunk cable 5 is attached.

However, the DPM 2 may also have its own display device embedded in it or associated with it and may be adapted to send/stream the standard ECG signal via a communications/data network to make the standard ECG signal available on a local/remote personal computer or portable device.

It should be noted that FIG. 1 illustrates a non-limiting example of implementation. Changes to the system 200 are possible without departing from the scope of the invention as defined in the claims. For example, although FIG. 1 illustrates cables for communicating the data between different modules, it is also contemplated that wireless connections may be used including but not limited to: Wi-Fi, Bluetooth etc.

Furthermore, the sensor array may be in a variety of other objects including: clothing, beds, and vehicle devices/components. In another example, the sensor array may be provided in a plurality of devices including but not limited to: furniture (e.g. chair, bed/mattress/cover, sofa, seat, mattress), in-vehicle devices (e.g. seat, headrest, steering wheel etc.), or in a wearable device (e.g. jacket, shirt, t-shirt, sweater, bra etc.).

Selection Algorithm

Traditional ECG dictates electrode locations that are based on physiology of the patient whereby traditional contact electrodes are adhered to these locations, maintaining relative body position regardless of the patient's movement. For example, the V1 electrode should be placed on the $4^{th}$ intercostal space to the right of the sternum, the RA electrode should be placed on the right arm, the LA electrode on the same location as the RA electrode but on the left arm the RL electrode should be placed on the right leg, lateral calf muscle and so on . . . as exemplified in FIG. 11. The importance of these electrodes and their locations lies in the fact that the difference in voltage between two specific locations represents a medically defined ECG lead (as discussed with respect to FIGS. 11 and 12), and the lead in electrocardiography represents a vector along which the heart's depolarization is measured and recorded to produce the electrocardiogram.

Therefore in order to produce an ECG signal that is compatible with traditional ECG standards it is necessary to follow the same principle although data is being collected in a contactless manner.

Figure 2:
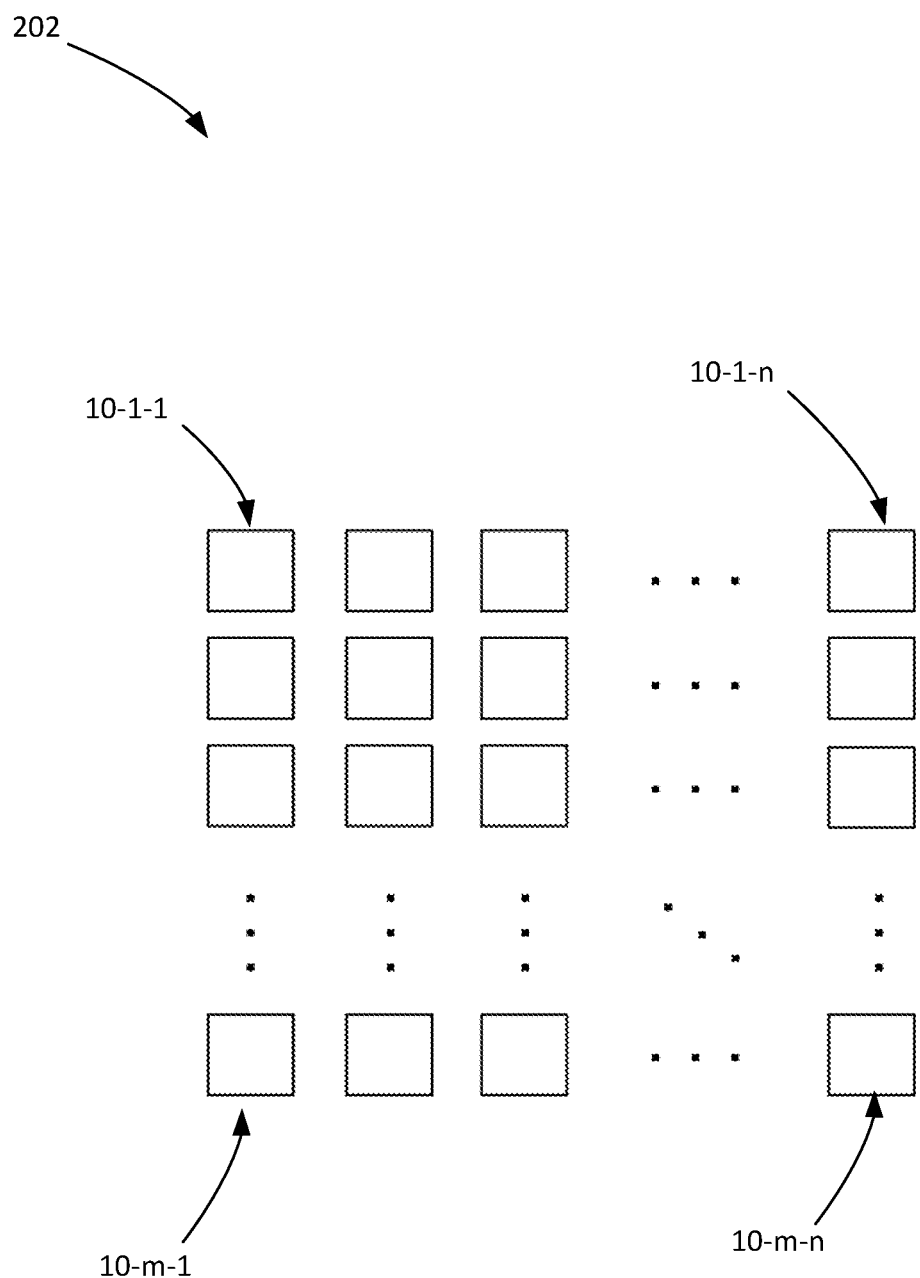
FIG. 2 illustrates a non-limiting example of a sensor matrix in accordance with an embodiment.

FIG. 2 illustrates a non-limiting example of a sensor matrix 202 in accordance with an embodiment. As shown in FIG. 2 the matrix 202 comprises n columns and m rows of sensors 10 arranged in a matrix configuration such that no matter how the patient is placed on the matrix 202, there would always be at least one sensor at a location on the patient's body that corresponds to the physical placement of a conventional ECG electrode. Using an adaptive algorithm embedded in the DPM 2, the matrix 202 may be used for obtaining a continuous ECG reading by selecting a given sensor 10 form the matrix 202 which corresponds to a defined ECG location on the patient's body.

Figure 3:
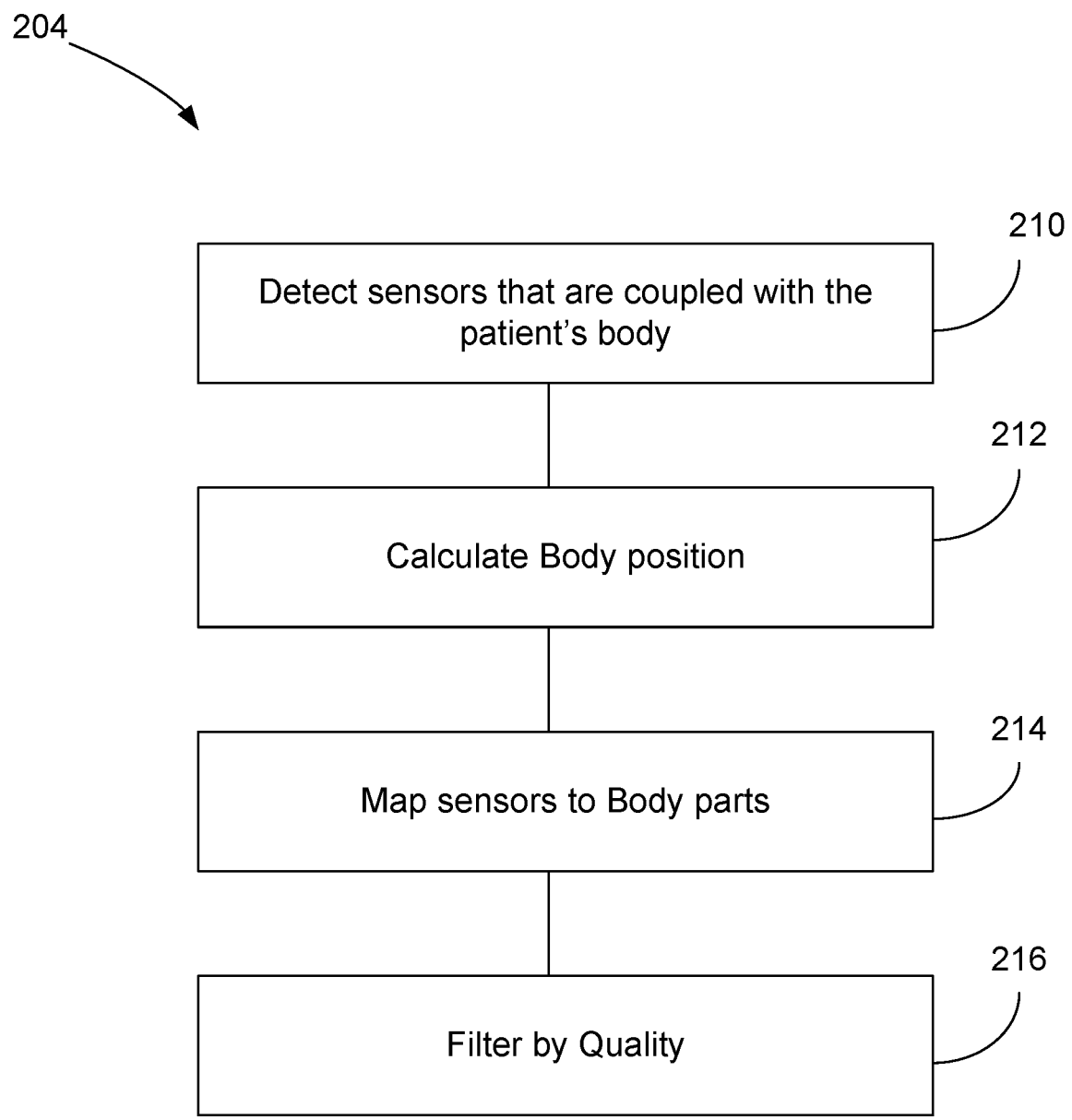
FIG. 3 is a flowchart illustrating the main steps performed by the selection algorithm, in accordance with an embodiment.

FIG. 3 is a flowchart illustrating the main steps performed by a selection algorithm 204, in accordance with an embodiment. At step 210 the algorithm detects which sensors 10 are in close proximity to the patient's body, by measuring the impedance between each sensor 10 and the patient. This allows for detecting the sensors 10 that can be used to obtain data from. ECG signals output by these sensors 10 (the ones determined to be in close proximity of the body) are then analyzed to obtain a body outline of the patient.

Figure 13A:
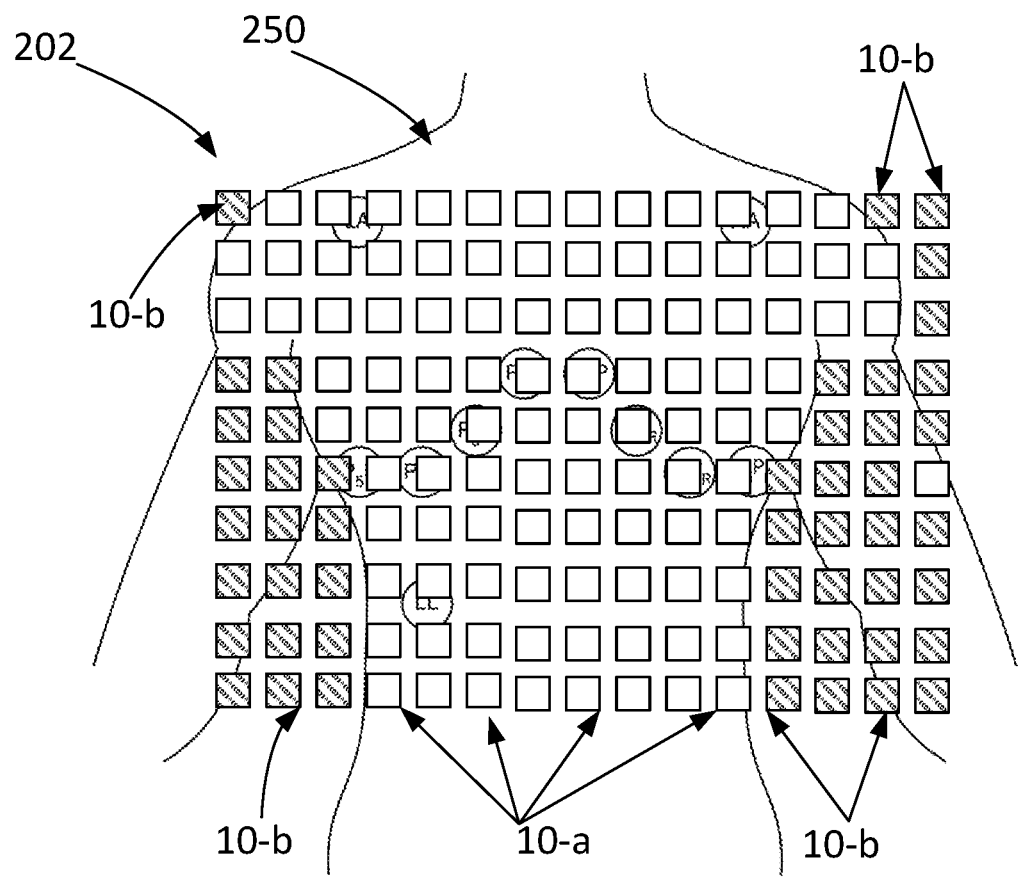
FIGS. 13a & 13b illustrate an example of how the system determines the body outline of the patient.
Figure 13B:
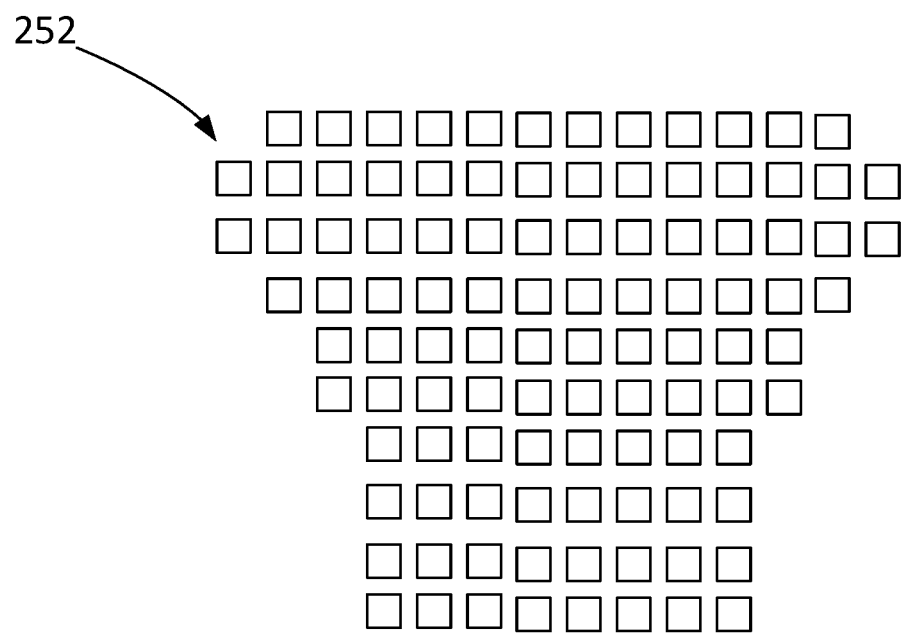

In a non-limiting example of implementation, the embodiments may use different types of information to obtain the body outline. The first type is the coupling impedance which represents the distance between the body and the sensor. When the coupling impedance is too high, the sensor is too far from the body and cannot be used. The second type is the signal itself e.g. morphology of the signal and how the signal looks like to see whether the signal has the usual ECG pattern or not (PQRSTU waveforms). The third type of information relates to the geometrical locations of the ECG sensors providing good ECG signals. These sensors and their location provide an indication on the geometrical shape of the human body as exemplified in FIGS. 13a and 13b. in the example of FIG. 13a, assuming that a user 250 is laying down on a mattress having the sensor pad 202 embedded therein, the sensors 10a that are in proximity of the patient's body will obtain a good ECG signals while the sensors 10b outside of the patient's body will not obtain a good signal. Based on this information and the location of each sensor on the pad 202, the DPM 2 may obtain an outline 252 of the patient's body from which the DPM may determine the shape, width and other dimensions of the patient's body as exemplified in FIG. 13b. Using this information and a set of rules embedded in the DPM 2, the DPM 2 may then detect/determine locations of body parts and associate one or more sensors 10 with each body part/body location for ECG purposes as discussed below.

At step 212 the algorithm analyses the ECG signal received from the sensors and combines it with the body outline already detected to find the position of the patient's body on the pad. At step 214 the algorithms performs a mapping of where on the body each sensor 10 is located using the information obtained from steps 210 and 212. Once groups of sensors are found to be near each major body part for ECG purposes (Right Arm, Left Arm, etc.), the signals from those adjacent sensors are compared and filtered at step 216 to select a single sensor with the best ECG signal to receive and record therefrom ECG data for that respective body part.

In an embodiment, the DPM 2 may be adapted to run the selection algorithm 204 continuously and dynamically in order to re-examine the readings obtained from the sensors 10 in real time to re-verify the selection of the sensor 10 having the best ECG reading to constantly take into consideration the patient's movement whereby a new sensor 10 may be selected which provides a better reading than the one previously selected before the movement.

In another embodiment, the system may detect when a patient moves and determines when it is necessary to run the algorithm again to recalculate whether or not a new selection needs to be made. For example, the system may monitor the signal's strength/quality and determine to re-run the selection algorithm 204 when the signal quality drops below a given threshold.

Detection of PQRSTU Waveforms

Figure 4:
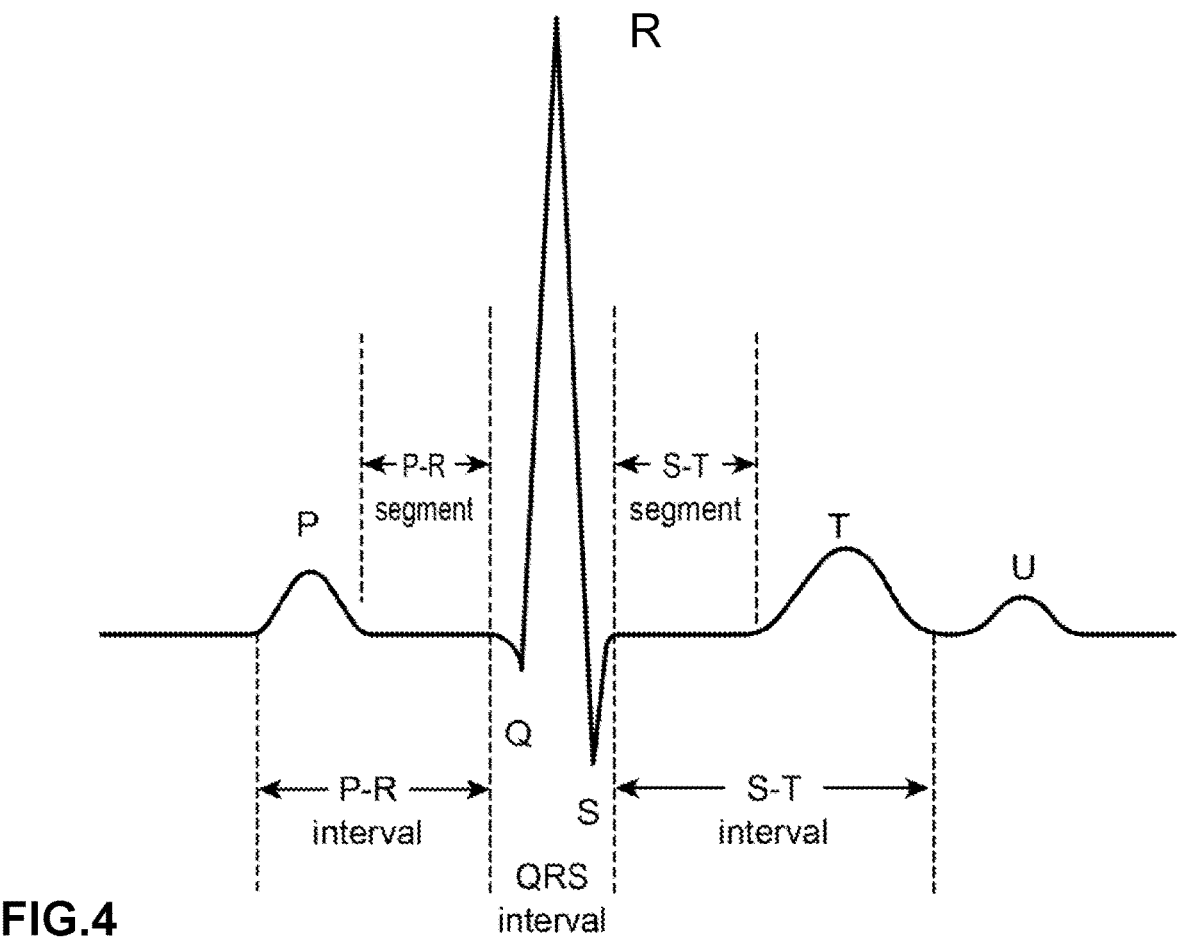
FIG. 4 illustrates an example of a full PQRSTU waveform obtained for a patient using a system in accordance with an embodiment.

As discussed above, the system may be configured to record cardiac electrophysiological activity and ECG. Specifically, the system may be designed to acquire the full PQRSTU spectrum constituent ECG waveforms as exemplified in FIG. 4 which illustrates an example of a full PQRSTU waveform obtained for a patient using a system in accordance with an embodiment. The PQRSTU waveforms illustrated in FIG. 4 are generated by the heart and captured by the system to be viewed by doctors for diagnosis. In an embodiment, the system captures the ECG readings and processes them to produce ECG signals that may be read and viewed using existing medical equipment and produces waveforms that are identical to those produced by standard contact ECG systems, and as such can be used in place of standard ECG systems for all applications.

Needless to say, the contactless sensors 10 do not produce an output that is compatible with existing medical equipment's (e.g. monitors and the like) and therefore cannot interface with these equipment, hence the need for further processing. In an embodiment, the DPM converts the acquired signal into a format that complies with the international standards for existing medical equipment. This allows for a seamless replacement of conventional contact ECG systems without the need to replace existing diagnostic medical devices or re-train doctors and medical professionals. Such conversion may be performed in the DPM 2 using a combination of digital signal processing and analog output circuitry in the Digital to Analog Converter stage (19).

Sensor Design

Figure 5:
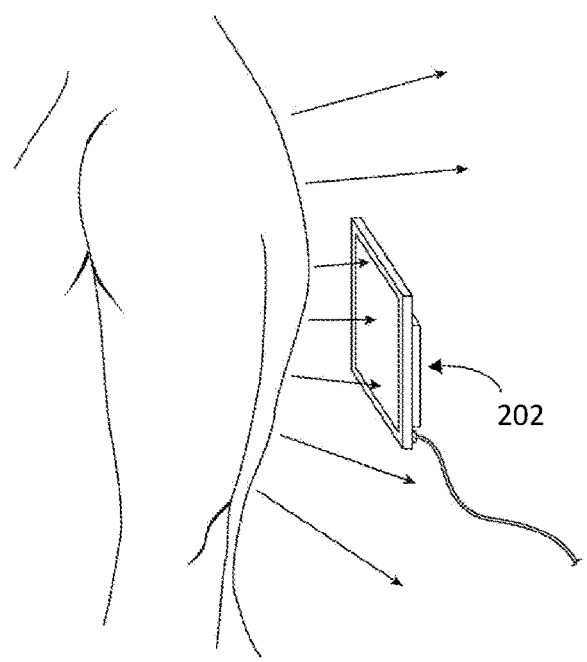
FIG. 5 illustrates how the senor array captures ECG signals without direct contact with the patient's skin.

As discussed above, the embodiments obtain ECG readings of the patient using contactless ECG sensors 10. The sensors 10 are specifically designed to capture high quality ECG from a patient without requiring direct electrical contact with the patient's skin. This allows to place the sensors 10 at some distance from the patient and/or to be separated from the patient's skin by a fabric such as clothing, bedding, etc. as exemplified in FIG. 5 which illustrates an example of how the senor array captures ECG signals without direct contact with the patient's skin.

Figure 6:
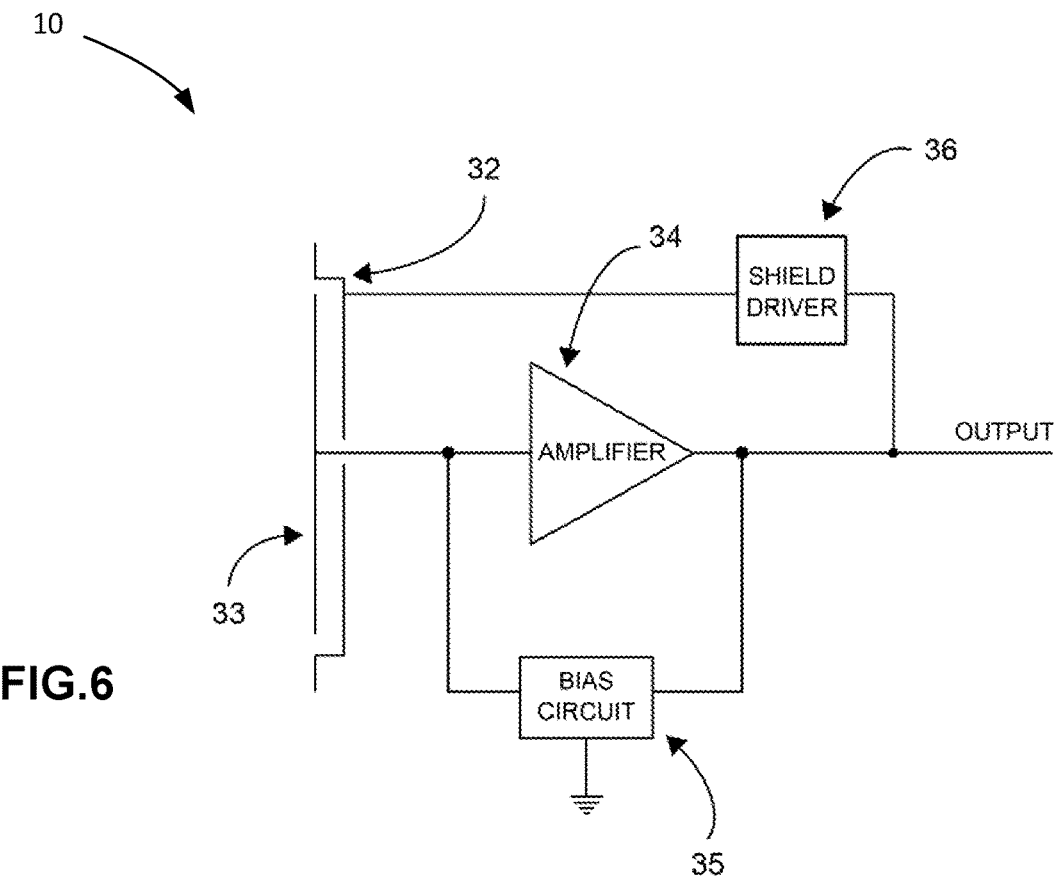
FIG. 6 is a block diagram illustrating an exemplary sensor design of a contactless ECG sensor, in accordance with an embodiment.

FIG. 6 is a block diagram illustrating an exemplary sensor design in accordance with an embodiment. As shown in FIG. 6 the sensor 10 may include a conductive electrode 33, an electrode shield 32, and an electrodynamic sensor including an amplifier 34 and a bias circuit 35 voltage. In the exemplary design of FIG. 6, the gain/current buffering amplifier 34 may be used in a type of negative feedback topology, and the input bias network 35 is adapted to increase the effective input impedance of the amplifier 34, to preserve the signal quality of the acquired ECG. The input of the electrodynamic sensor is connected to the conductive electrode 33. A shield driving circuitry (36) may be employed to generate a feedback signal to connect to the electrode shield (32) to further increase the signal to noise (SNR) ratio by reducing parasitic capacitance seen at the input of the electrodynamic sensor.

The electrode 33 may be capacitively coupled to the patient's body by being in proximity to, but not touching the skin/body. This can be accomplished by laying on a bed with an array of sensors 10 embedded in it (as non-limiting example of implementation), while clothed. The electric field near the surface of the patient's skin that is created from the electrical activity of the heart capacitively induces a charge on the conductive electrode 33 without direct electrical contact. This charge may then be collected and amplified by the electrodynamic sensor, which produces an electrical signal (voltage) that is representative of the electrical activity of the heart in that location (complete PQRSTU).

The electrode shield 32 is configured to reduce the amount of stray interference that the electrodynamic sensor receives and also decrease the effective capacitance of the input of the amplifier 34, which helps to preserve signal quality of the acquired ECG.

In an non-limiting example of implementation, both the electrode 33 and the electrode shield 32 may be made of an elastic/flexible material which allows the sensor 10 to better adapt to the geometry of the human body and obtain better ECG readings. At the same time this configuration allows the sensors 10 to be seamlessly provided in the fabric (or any of the following: gel/silicone/rubber type pad/mat etc.) in which the sensor array is to be placed.

Figure 7:
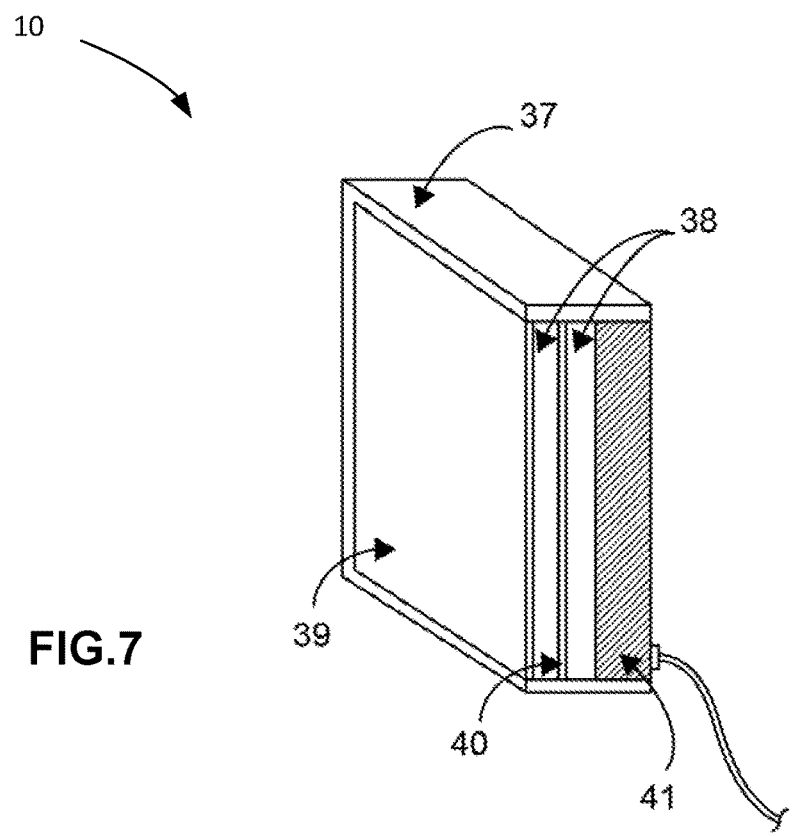
FIG. 7 illustrates an example of a physical design of a contactless ECG sensor, in accordance with an embodiment.

FIG. 7 illustrates an example of a physical design of the sensor 10. As exemplified in FIG. 7, the physical design includes the conductive electrode 33 physically implemented as a layer 39, the shield 32 physically implemented as the layer 40, and the remaining of the circuitry embedded in the layer 41. The entire structure may be produced on a substrate 37 which may also be a printed circuit board, for example. In the design illustrated in FIG. 7, the layers 39, 40 and 41 may be insulated from each other by dielectric layers 38 to provide electrical insulation.

Figure 8:
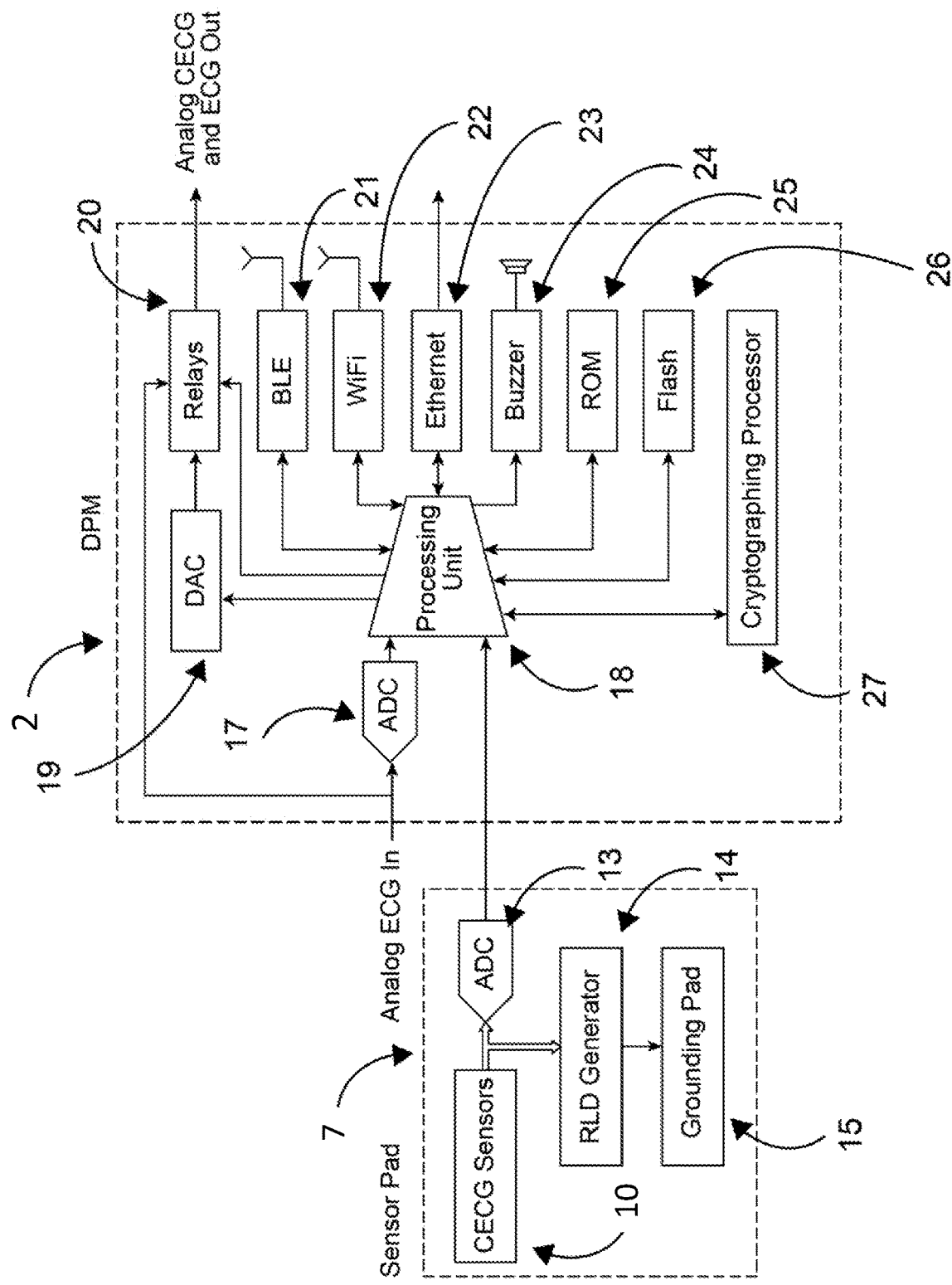
FIG. 8 illustrates an exemplary block diagram of an overall design of a system in accordance with an embodiment.

FIG. 8 illustrates an exemplary block diagram of an overall design of a system in accordance with an embodiment.

Referring to FIG. 8, and as discussed above with respect to FIG. 1, the system may include a sensor pad 7 comprising contactless ECG sensors (hereinafter CECG sensors 10) which may be provided in the form of an array 202 such as that shown in FIG. 2. The sensor pad 7 may also include a grounding pad 15, a driving circuitry e.g. a right leg drive (RLD) generator 14 (discussed below), and an ND converter 13. The sensor pad 7 outputs the digitized ECG readings of the sensors 10 to the DPM 2. The RLD generator 14 is configured to feed the grounding pad 15 with a high frequency signal that is outside of the ECG frequency band. This high frequency signal is then coupled through the patient's body to the CECG sensors, where the amplitude is recorded and analyzed by the DPM 2. This gives the system a metric of how well-coupled each sensor is to the patient, effectively an impedance measurement to determine what the signal quality is from each sensor.

In addition to the digitized CECG sensor data, the DPM 2 may also be configured to receive standard ECG data of conventional electrodes in an analog format. Such analog ECG data is optionally acquired through the use of standard contact electrodes and a trunk cable (5). The analog signals may be converted using an ADC 17. The signals may then be filtered using a digital signal processing unit 18, and output over a variety of wired and wireless interfaces (Wi-Fi (22)/Ethernet (23) to a mobile app (3)/cloud server (4) and through the 'Analog CECG & ECG out' interface to existing medical equipment (6)).

The DPM 2 may include some sort of non-volatile memory e.g. flash memory 26 for storage of ECG data (if necessary). The DPM 2 may also be configured to perform diagnosis for acute issues, and send a warning over any one of the communication interfaces or an integrated sound alarm (24). The DPM 2 may also include a Bluetooth Low Energy interface (21) to enable configuration by the user through a mobile device. A Read Only Memory (25) may also be included to store a unique identifier. A Cryptographic processing module (27) may also be used to encrypt and decrypt data transmitted/received through the communication interfaces, and securely stores keys for this data encryption.

All sensor data (contactless and contact) can be sent over the wired and wireless interfaces. The selection algorithm 204 (discussed above in FIG. 3) decides which sensor information should be output over the analog interface 19 to existing medical equipment. A relay 20 may be provided to switch between the analog data received from the conventional electrodes and the contactless sensors 10 and to allow the DPM 2 to compare between the two. In DPM 2 can be configured to be turned off to act like a pass-through cable, without affecting the contact ECG signal if desired (controlled by the Processing Unit and Relays (20)). It can also be used in 'hybrid mode', during which a combination of CECG and ECG sensors can be output over the analog interface, if it improves the quality of the ECG signal.

Automatic Gain Correction

Figure 9:
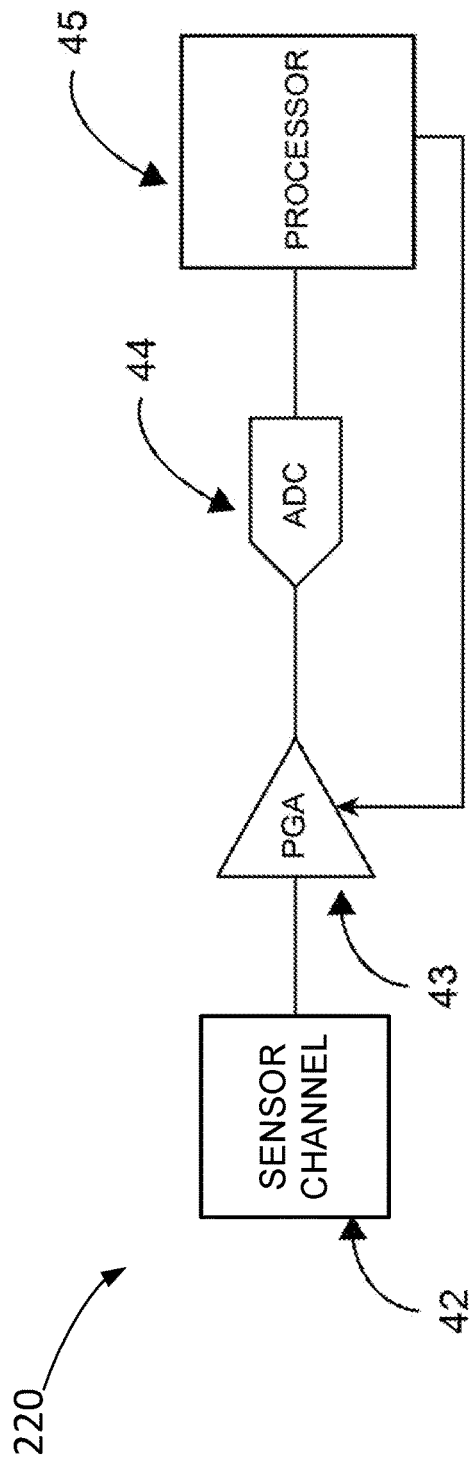
FIG. 9 is a block diagram illustrating an exemplary gain control mechanism, in accordance with an embodiment.

Due to the large, yet finite, input impedance of the electrophysiological sensors 10, variations in the capacitive coupling between each sensor 10 and the patient's body (e.g. changes in the distance between each sensor and the body) can cause variations in the gain of each sensor channel. This has the effect of affecting the amplitude of ECG leads, in the same way that a dried out contact adhesive electrode produces a lower quality signal than a new one. To address the problem, a gain control mechanism is provided which allows the system to control relative impedance differences between different contactless ECG sensors, and an absolute impedance between each contactless ECG sensor and the human body due to a difference in distance between each contactless ECG sensor and the human body. As shown in FIG. 9, a programmable gain amplifier 43 (either in the analog or digital domains) may be provided on each sensor channel 42 to offset the change in gain caused by differences in coupling between the sensors 10 and the patient. FIG. 9 is a block diagram illustrating an exemplary gain control mechanism in accordance with an embodiment. As shown in FIG. 9, the gain control mechanism 220 may include a feedback loop including an ADC 44 coupled between the PGA 43 and a processor 45 which itself is connected to the PGA 43 to control its gain in real-time as the change is occurring.

The processor 45 may be a dedicated processor and may also be a processor module embedded into the processing unit 18 of the DPM 2.

Right Leg Drive

Referring back to FIG. 8, a grounding pad 15 is shown which in operation should be placed near, but not in contact with (at a distance), the patient's body. This pad is driven with a feedback signal derived from the ECG signals to provide a capacitively coupled ground reference to the patient's body. The feedback signal is derived in such a way to increase the common mode rejection ratio (CMRR) of the system (by over 10 dB, typically). This reduces interference from common mode signals and preserves the signal quality of the acquired ECG.

Figure 10:
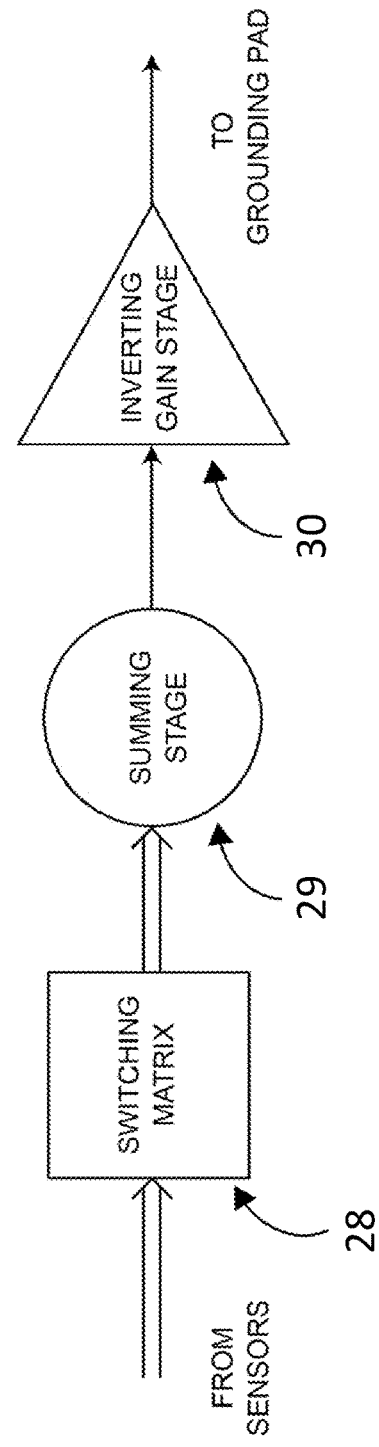
FIG. 10 is an exemplary block diagram illustrating the function of the RLD generator, in accordance with an embodiment.

FIG. 10 is an exemplary block diagram illustrating the function of the RLD generator 14, in accordance with an embodiment. As shown in FIG. 10, data received from the sensors is selected (or discarded) using a switching matrix (29) which selects specific sensors 10 to obtain data from using an RLD algorithm implemented digitally in the processing unit (18). The signals are then summed (29), inverted and amplified (30). This constitutes the driving signal for the grounding pad 15.

The RLD algorithm is configured to monitor the common mode signal acquired from each sensor (and by extension, the ECG signals output from selection algorithm). The RLD algorithm may select the set of sensors that increases the common mode rejection ratio of the system after the RLD signal is applied to the patient in the feedback configuration.

Acquired Leads

As discussed above, the ability to compare a current ECG to an old one is of an immense medical value and this is not possible with existing systems which do not allow for long term monitoring. For example, an abnormal ECG does not prove acute cardiac disease, and a normal ECG does not exclude cardiac disease. It is therefore necessary to compare new ECG with ECG's made in the past. Hallmarks may include Is there a change in rhythm?
Is there a change in frequency?
Is there a change in conduction time?
Is there a change in heart axis?
Are there new pathological Q's?
Is there a change in R wave size?
Is there a change in ST?
Is there a change in T wave?

The above changes immediately result in further investigations. Changes in the electrocardiogram can be further classified as acute and chronic, however, both require comparison electrocardiograms.

In general, as the number of electrodes used increases, the monitoring time that is possible decreases. Currently, one major limitation of the current standards is the difficulty in obtaining long term monitoring with multiple electrodes due to the inherent limitation of placing multiple electrodes and maintaining them on the body.

Figure 11:
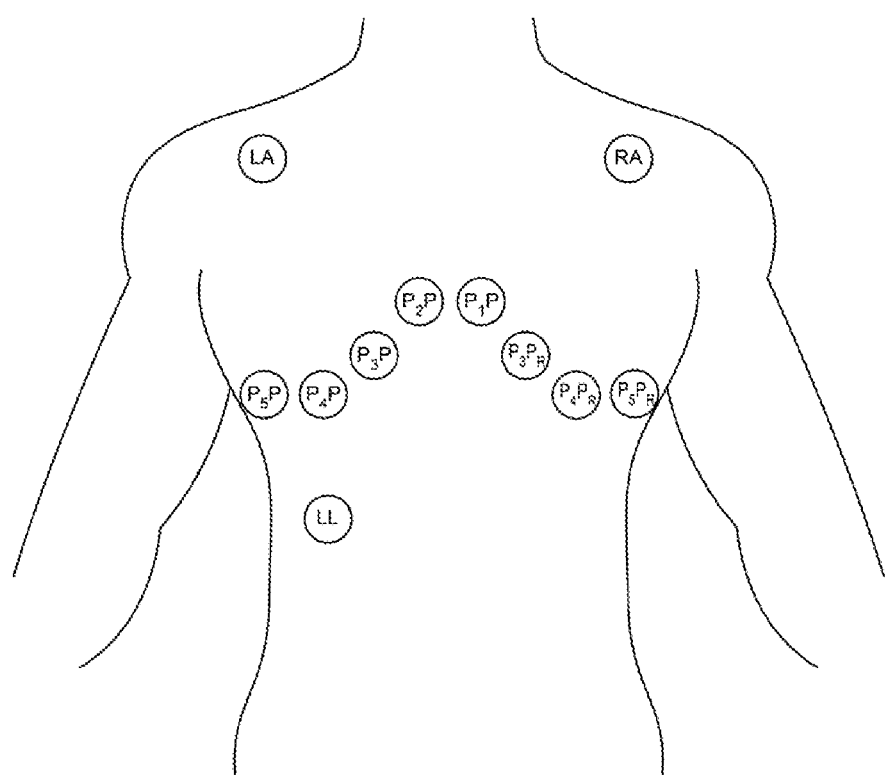
FIG. 11 shows medically recognized ECG locations for obtaining standard ECG leads.
Figure 12:
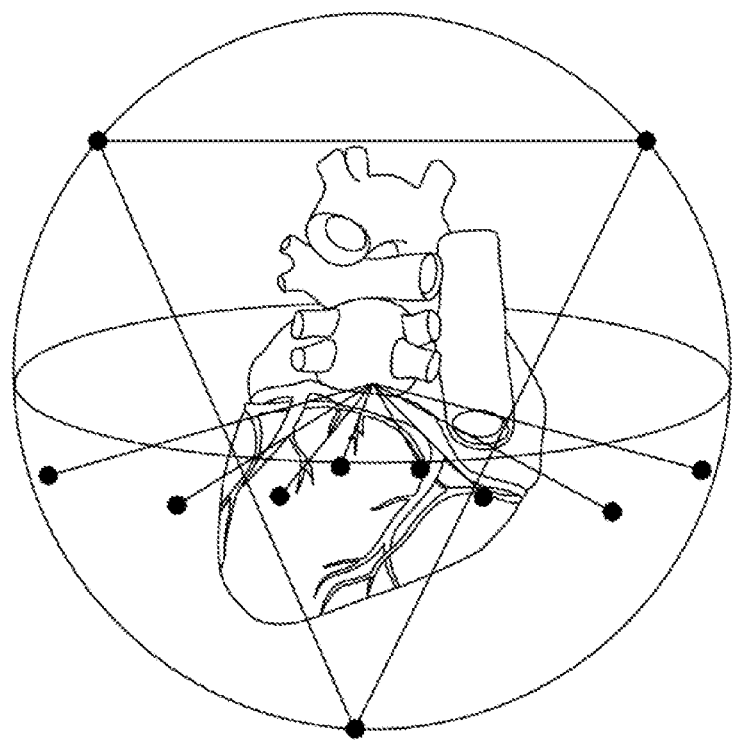
FIG. 12 illustrates an example of standard ECG leads, each lead being shown as a vector between two locations on the human body.

The system described above allows for serial comparison of electrocardiograms for the first time. The system has proven to acquire posterior ECG leads. According to a modified Mason-Likar lead system, a 16 lead ECG can be acquired from the patient laying on the matrix of sensors, embedded in a mattress, chair, etc. The acquired leads include: Leads I, II, III, aVr, aVl, aVf, V1, V1R, V2, V2R, V3, V3R, V4, V4R, V5, V5R as exemplified in FIG. 11 and FIG. 12. FIG. 11 shows medically recognized ECG locations for obtaining standard ECG leads, and FIG. 12 illustrates an example of standard ECG leads, each lead being shown as a vector between two locations on the human body.

The pad including the sensors 10 can be placed, unperceivably under a mattress so that ECG data can be acquired from posterior leads; e.g. the prone position. The system may be based on the Mason-Likar sensor placement used for the acquisition of the ECG during stress testing. Standard 12 lead ECG placement is not used because of myopotentials, motion, artifacts, etc. and is limited to the 10 second 12 lead ECG printout and is not practical for short to long term monitoring.

Posterior placed electrodes are an accepted method of ECG acquisition, and indeed are used as an adjunct in certain situations to the more commonly used method of anterior lead placements. Anterior lead placement is currently the only type of lead placement used because of convenience. However, prone position ECG leads are performed in certain situations with standard electrodes, but because of the inherent difficulties, is not a standard.

Figure 14:
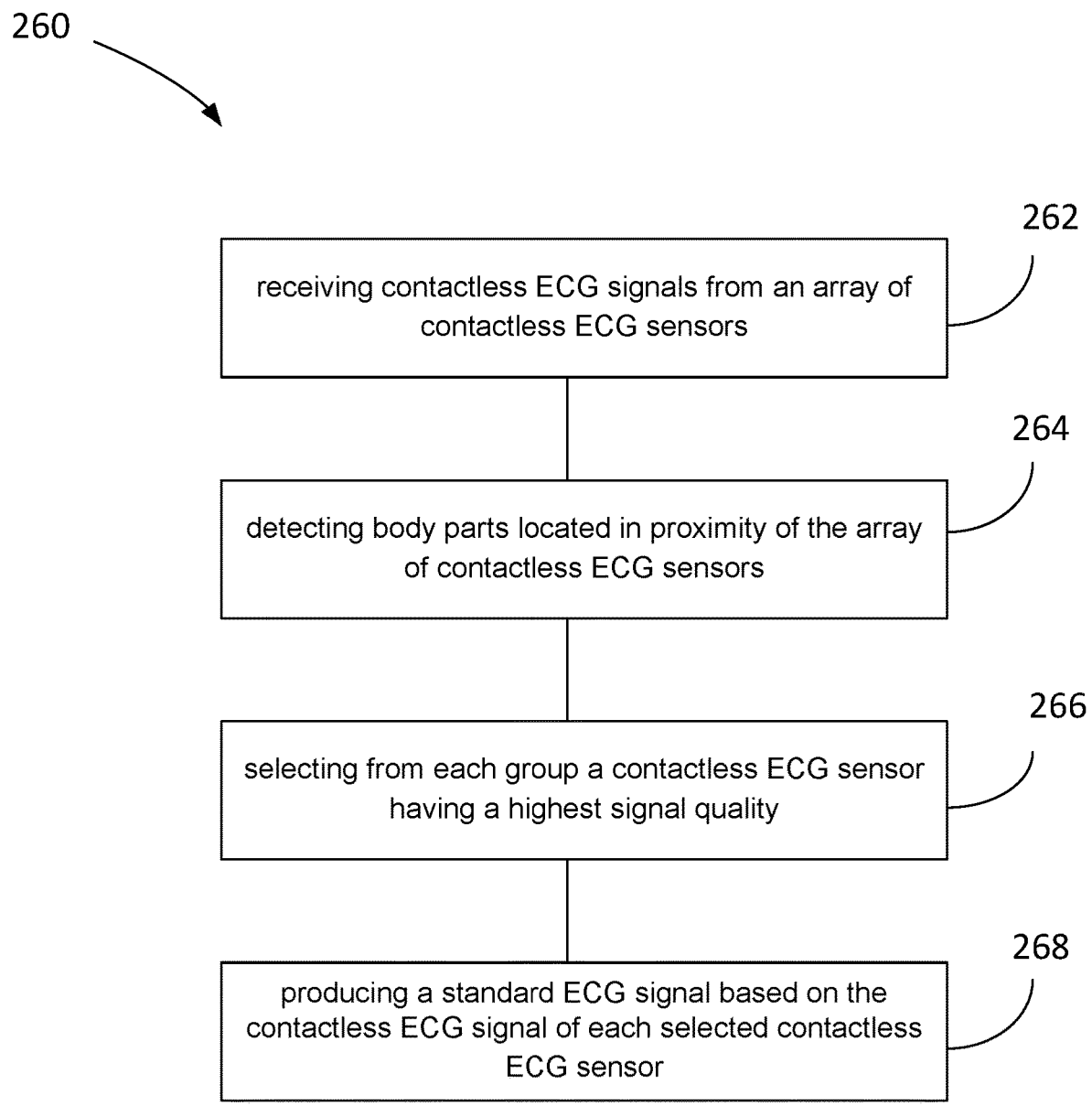
FIG. 14 is flowchart of a method for providing electrocardiogram (ECG) signals for a human body using contactless ECG sensors.

FIG. 14 is a flowchart of a method for providing electrocardiogram (ECG) signals for a human body using contactless ECG sensors. As shown in FIG. 14, the method 260 begins at step 262 by receiving contactless ECG signals from an array of contactless ECG sensors. Step 264 comprises detecting body parts located in proximity of the array of contactless ECG sensors. Step 266 comprises selecting from each group a contactless ECG sensor having a highest signal quality. Step 268 comprises producing a standard ECG signal based on the contactless ECG signal of each selected contactless ECG sensor.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for generating electrocardiogram (ECG) signals for a human body using contactless ECG sensors, the method comprising:
   receiving contactless ECG signals from an array of contactless ECG sensors;
   detecting one or more body parts located in close proximity of the sensor array;
   selecting for the detected body parts contactless ECG sensors providing the highest signal quality; and
   producing a standard ECG signal based on the contactless ECG signals received from the selected contactless ECG sensors associated with the detected body parts;
   the method further comprising obtaining an outline of a portion of the human body detected by the sensor array, and detecting the one or more body parts in the body outline using a set of rules.

2. The method of claim 1, further comprising identifying the contactless ECG sensors that are located in close proximity to the human body by measuring an impedance between each contactless ECG sensor and the human body.

3. The method of claim 1, further comprising associating, to each detected body part, a group of contactless ECG sensors that are detecting that body part, and selecting from that group the contactless ECG sensor providing the highest signal quality for that body part.

4. The method of claim 1, further comprising selecting another contactless ECG sensor for one or more body parts following a movement of the human body with respect to the array of contactless ECG sensors.

5. The method of claim 1, further comprising: repeating the steps of detecting and selecting continuously for selecting another contactless ECG sensor for a given body part following a movement of the human body with respect to the array of contactless ECG sensors.

6. The method of claim 1, further comprising continuously monitoring a current signal quality of the selected contactless ECG sensor associated with each body part to select another contactless ECG sensor when the current signal quality drops beyond a given threshold.

7. The method of claim 1, further comprising providing an automatic gain control mechanism adapted for controlling one or more of: a relative impedance differences between different contactless ECG sensors, and an absolute impedance between each contactless ECG sensor and the human body due to a difference in distance or type of clothing material between each contactless ECG sensor and the human body.

8. The method of claim 1, further comprising providing a grounding pad in proximity of and at a distance from the human body, the grounding pad being adapted to provide a capacitively coupled ground reference to the human body for reducing interference.

9. The method of claim 8, further comprising feeding the grounding pad with a high frequency signal that is outside of an ECG frequency band for determining the capacitively coupled ground reference for each contactless ECG sensor.

10. The method claim 1, wherein the contactless ECG sensor is made of a flexible material and/or embedded in a fabric.

11. A device for generating electrocardiogram (ECG) signals for a human body, the device comprising a processor adapted to operably connect to a sensor array including a plurality of contactless ECG sensors to receive a plurality of contactless ECG signals for the human body, the processor being adapted to detect one or more body parts in close proximity of the sensor array, and select for the detected body parts contactless ECG sensors having the highest signal quality, the processor being adapted to produce a standard ECG signal based on the contactless ECG signals received from the selected contactless ECG sensors associated with the detected body parts; wherein the device is adapted to obtain an outline of a portion of the human body detected by the sensor array, and detect the one or more body parts in the body outline using a set of rules.

12. The device of claim 11, wherein the device is adapted to associate, to each detected body part, a group of contactless ECG sensors that are detecting that body part, and select from that group the contactless ECG sensor providing the highest signal quality for the body part.

13. The device of claim 11, wherein the device is adapted to continuously monitor a current signal quality of each selected contactless ECG sensor associated with each detected body part to select another contactless ECG sensor when the current signal quality drops beyond a given threshold.

14. The device of claim 11, wherein the device identifies the contactless ECG sensors that are located in close proximity to the human body by measuring an impedance between each contactless ECG sensor and the human body.

15. The device of claim 11, wherein the device is adapted to select another contactless ECG sensor for one or more body parts following a movement of the human body with respect to the array of contactless ECG sensors.

16. The device of claim 11, further comprising a grounding pad in proximity of and at a distance from the human body, the grounding pad being adapted to provide a capacitively coupled ground reference to the human body for reducing interference.

17. The device of claim 16, wherein the grounding pad is fed with a high frequency signal that is outside of an ECG frequency band for determining the capacitively coupled ground reference for each contactless ECG sensor.

18. The device of claim 11, wherein the contactless ECG sensor is made of a flexible material and/or embedded in a fabric.

\* \* \* \* \*